United States Patent [19]

Heller et al.

[11] Patent Number: 4,859,583

[45] Date of Patent: Aug. 22, 1989

[54] CHEMILUMINESCENT IMMUNOCHEMICAL TECHNIQUE FOR LOW MOLECULAR WEIGHT ANTIGENS

[75] Inventors: Michael J. Heller, Poway, Calif.; Larry E. Morrison, Lisle, Ill.

[73] Assignee: Amoco Corporation, Chicago, Ill.

[21] Appl. No.: 705,493

[22] Filed: Feb. 25, 1985

[51] Int. Cl.$^4$ .................. G01N 33/53; G01N 21/00
[52] U.S. Cl. .......................... 435/7; 422/52; 422/61; 422/102; 435/14; 435/18; 435/27; 435/28; 435/810; 436/501; 436/518; 436/807; 436/810
[58] Field of Search ............ 422/52, 61, 102; 435/4, 435/7, 14, 27, 810, 18, 25, 28; 436/50, 518, 807, 810

[56] References Cited

U.S. PATENT DOCUMENTS

| | | | |
|---|---|---|---|
| 4,433,060 | 2/1984 | Frenzel | 436/518 |
| 4,446,232 | 5/1984 | Liotta | 436/535 |
| 4,477,576 | 10/1984 | Deutsch et al. | 436/500 |
| 4,495,151 | 1/1985 | Ohyama et al. | 422/102 |
| 4,522,923 | 6/1985 | Deutsch et al. | 436/536 |
| 4,594,326 | 6/1986 | Wade | 436/514 |
| 4,613,567 | 9/1986 | Yasoshima et al. | 436/535 |
| 4,615,983 | 10/1986 | Koyama | 436/535 |
| 4,626,513 | 12/1986 | Burton et al. | 436/535 |
| 4,632,901 | 12/1986 | Valkirs et al. | 436/518 |

Primary Examiner—Christine M. Nucker
Attorney, Agent, or Firm—Anthony J. Janiuk; William H. Magidson; Ralph C. Medhurst

[57] ABSTRACT

A sample device and method for assaying samples containing members of immunological pairs by chemiluminescence include a first chamber wherein antibody-conjugated reagent antigen labelled with a chemiluminescence moiety is displaced from the antibody by sample antigen. The labelled reagent antigen diffuses into a second chamber, wherein the chemiluminescence moiety reacts with cofactors to produce a light emission proportional to the amount of sample antigen present.

37 Claims, 3 Drawing Sheets

CHEMILUMINESCENT IMMUNOCHEMICAL TECHNIQUE FOR LOW MOLECULAR WEIGHT ANTIGENS

BACKGROUND OF THE INVENTION

1. Field of the Invention

This invention relates to devices and methods for assaying antigens in a fluid sample. More particularly, it relates to a light-emitting assay for antigens having one binding site for antibodies.

2. Description of the Prior Art

Assays directed to detection and quantification of physiologically significant materials in biological fluid and tissue samples are important tools in scientific research and in the health care field. Immunoassays detect the reaction between immunological pairs, antibodies (Ab) and antigens (Ag), as set forth below:

Antibodies and antigens have complementary surfaces or cavities which specifically bind to a particular spatial and polar organization of the other molecule. The binding is reversible and antibodies and antigens may compete for limited binding sites. In typical assays, either the antigen, antibody or both may be labelled with an indicator molecule. The analyte of interest is most often the antigen; however, either antigen or antibody may be the object of the assay.

Several different types of assays have been developed which are capable of detecting relatively concentrated components of common biological samples such as human serum. Such assays include high-resolution agarose gel electrophoresis and test procedures based on the catalytic activity of endogenous enzymes. These methods generally do not have the sensitivity required to detect and quantify the numerous other physiologically important sample constituents which may be present at very low concentrations. Important constituents include endogenous molecules intimately involved in cellular regulation (hormones, steroids, biochemical messengers); basic structural components of the organism (amino acids, proteins, polysaccharides); genetic material (DNA, RNA); vitamins, drugs and drug metabolites; toxins, pathogens and substances generated by the immune system.

The early biological assay techniques for the clinically important serum constituents, such as the immunoprecipitation and immunodiffusion techniques developed in the 1940s, also lacked the sensitivity necessary to detect and quantify most serum constituents of medical interest. In 1956, Berson and Yalow reported detection of soluble insulin-antibody complexes in the serum of insulin-treated diabetics injected with radiolabelled preparations of the serum hormone. (See Berson et al., *J. Clin. Invest.* 35, 170 (1956).) The principles of this assay, commonly referred to as radioimmunoassay (RIA), were subsequently established and by the late 1960s the RIA was a major tool in endocrine laboratories. For example, virtually all the information now known about peptide hormonal physiology has resulted from the introduction of RIA and its ability to detect $10^{-10}$ to $10^{-12}$ molar concentrations of hormones.

The RIA assay technique was subsequently shown to be applicable to quantitative detection of any substance for which a specific antibody can be prepared, permitting development of a host of RIAs for chemical compounds such as drugs. In a broader sense, the RIA principle has also been extended to systems in which other binding substances replace antibody, for example, in receptor assays. In 1980, the sales of immunodiagnostic reagents alone were estimated to be $229 million.

Although exhibiting the desired sensitivity, RIAs have several disadvantages inherent in the required reagents. The use of radioactive isotopes requires a special permit and a special laboratory. For this reason, RIAs are performed by personnel separate from those in the routine clinical chemistry laboratory. Radiation can cause health hazards particularly for those working with the commonly used isotopes of iodine. In addition, the useful lifetime of the radiolabelled reagents employed is limited by half-life of the isotopes and the destructive processes that occur during isotopic decay. The equipment used to determine the amount of radioactivity in the samples is expensive and the counting of a series of samples is relatively time-consuming. (See Smith et al., *Amer. Clin. Biochem.* 18, 253-74 (1981).) Overall, the amount of automation in the immunodiagnostic area is much less than that found in the routine clinical laboratory. Using an eight-hour polyethylene glycol accelerated second antibody RIA for separation of free from bound antigen, only about 75-90 assays can be performed daily by a single technician employing manual pipettes and a single-channel gamma counter.

To overcome the problems associated with RIA, immunoassay techniques employing nonisotopic labels have been developed. These nonisotopic assays, referred to as enzyme-linked immunoabsorbent assays (ELISA), fluoroimmunoassays (FIA), and luminescent immunoassays (LIA), depending upon the label employed, avoid many of the problems associated with RIAs and possess sensitivities near to that of the RIA. More recently, enzyme-linked assays have become increasingly popular and are replacing RIAs in many cases due to their more simple protocol relative to RIAs. As many as 2,000 assays per day can be run by a technician employing a solid-phase ELISA in microtiter plates with manual pipettes. These types of assays also have permitted the development of "homogeneous" immunoassays in which the bound and free labelled material need not be separated prior to the detection and measurement step. The RIA procedure requires the separation of free from bound labelled material for estimation of the target substance concentration, a "heterogeneous" system. Sensitive assays in which antigen-antibody reactions could be detected without separation of free from complexed antigen are also more simple to automate.

A typical nonisotopic heterogeneous assay procedure in which the analyte is a member of an immunological pair may include contacting an immobilized reagent member of an immunological pair specific to the analyte with a sample potentially containing the analyte allowing the sample analyte member to bind with the reagent member. The unbound sample members are then physically separated from the immobilized reagent members. If the sample analyte members are labelled with a detectable agent, or if the reagent members have labelled opposite reagent members competing for the same binding sites as the analyte member, the concentration of analyte can be determined by an increase or decrease in the detection of the label agent.

A typical nonisotopic homogeneous assay may include reagent including both members of the immunological pair. The reagent immunological pairs interact to produce a detectable signal. The introduction of a sample containing the analyte member of the immunological pair causes a modulation of the signal produced by the reagent immunological pairs. The change in the signal corresponds to the concentration of the analyte member in the sample.

Although superior to RIAs in several respects, the nonisotopic assays described above also exhibit problems caused by endogenous interfering factors present in the reaction mixture. Proteins and other components commonly found in serum samples may exhibit fluorescent, chemiluminescent and enzymatic activity similar to that of the employed label. In addition, the activity of these labels may be inhibited by the presence of endogenous compounds which absorb or scatter the emitted light of photophore labels, similarly colored compounds relative to chromaphore labels, and catalytic enzymes which degrade enzyme labels. Determination of the activity of the employed label may also be impaired by the turbidity of the sample as in the case of whole blood samples. To a certain extent, these problems may be minimized by assay techniques employing a separation step wherein bound labelled material is separated from the sample, washed with buffer and the label activity is thereafter determined, or wherein the separation of bound and unbound labelled material is achieved by partitioning them between immiscible aqueous phases. See Mattiasson et al., *Advances in Applied Microbiology* 28, 117–47 (1981) and U.S. Pat. No. 4,312,944.

However, there exists in the art a need for a sample device and method for assaying small antigens and/or antibodies by nonisotopic means, particularly chemiluminescence which is adaptable to automated procedures and which will function in turbid samples without separation steps.

DESCRIPTION

It is an object of the present invention to provide a sample device for assaying low molecular weight antigens and/or antibodies which is adaptable to automated techniques and is functional with turbid sample solutions. However, those skilled in the art will readily recognize that embodiments of the present invention have application in the assay of multi-epitopic antigens as well. The present invention is also applicable to any molecular species for which there exists another molecular species which selectively acts as a receptor, such as DNA, RNA, drug entities, and the like.

Other objects, features and advantages will be apparent to those individuals skilled in the art upon reading the following detailed description and examining the drawings.

For purposes herein, low molecular weight antigens and/or antibodies are those antigens and/or antibodies which have only one binding site for conjugation with their corresponding opposing member. Such antigens with low molecular weight include a large number of drugs and hormones such as Phenytoin, Digoxin, Quinidine, Gentamicin, and Thyroxine.

For the purpose of the present application, a member of an immunological pair refers to either an antibody or an antigen. If the term "member" pertains to an antibody, the terms "opposing" or "complementary member" refer to the respective antigen. If the term "member" refers to an antigen, the terms "opposing" or "complementary member" refer to antibody. Similarly the term "ligand" will be applied to one member of a pair of molecules which selectively bind together, and the terms "antiligand" or "receptor" will refer to the opposing member.

A label agent refers to any suitable agent or moiety which participates in a reaction in the presence of another moiety or agent. Moreover, embodiments of the present invention are applicable to label agents or moieties which participate in light-producing reactions in the presence of a bioluminescence or chemiluminescence cofactor. In the present application, for purposes of example and without limitation, a preferred embodiment will be discussed in terms of chemiluminescence label agents and cofactors. The moiety affixed to the reagent antigens will be referred to as the "label" or "label agent". For purposes herein, "cofactor" is broadly used to describe any chemical species, other than the label agent, which participates in a reaction which produces a detectable response. Chemiluminescence labels and cofactors produce a light response; however, other label agents and cofactors may, for example, produce a change in color, acidity or generate reactants which can be detected.

Examples of suitable chemiluminescence label agents include peroxidase, bacterial luciferase, firefly luciferase, functionalized iron-porphyrin derivatives, isoluminol and others. Choice of the particular chemiluminescence moiety for use as a label depends upon several factors which include the cost of preparing labelled members of the immunological pair, the method to be used for covalent coupling to the immunological member, and the size of the immunological member and the label. Correspondingly, the choice of chemiluminescence cofactors will depend upon the particular chemiluminescence moiety being used as the label.

Bioluminescent and chemiluminescent reactions have been intensely studied and are well documented in the literature (*Methods in Enzymology*, Vol. VLII, M. A. Deluca (Ed.), 1978). For example, the following reaction illustrates how light is emitted in the presence of a peroxidase catalyst:

$$H_2O_2 + \text{Luminol} \xrightarrow{\text{Peroxidase}} \text{Oxyluminol} + H_2O + N_2 + h\nu \quad (1)$$

Peroxidase is well suited for attachment to the reagent antigen for use as a label. The chemiluminescence cofactors effective for inducing light emission in the first reaction would then comprise hydrogen peroxide and luminol. Procedures for labeling antibodies or antigens with peroxidase are known in the art and are set forth in an article by J. Carlsson, H. Drevin, and R. Axen, *Biochem. J.*, 173, 723–737 (1978), which is incorporated by reference herein.

For example, to prepare peroxidase-labelled antibodies or antigens, peroxidase and antigens or antibodies are each reacted with N-succinimidyl 3-(2-pyridyldithio) proprionate (hereinafter SPDP) separately. SPDP-labelled peroxidase, or SPDP-labelled antigen or antibody is then reacted with dithiothreitol to produce thiol-labelled peroxidase, or thiol-labelled antigen or antibody. The thiol derivative is then allowed to couple with the SPDP-labelled antigen or antibody, or SPDP-labelled peroxidase. The following detailed description is typical: 12.6mg of (Goat) anti-rabbit IgG in 2 ml of phosphate buffered saline (hereinafter PBS) (0.15m sodium chloride, 0.02M sodium phosphate, pH 7.5) were combined with 23.5 μl of 20mM SPDP in ethanol.

The solution was stirred gently at room temperature for one hour and then purified on a Sephadex G-25 column, eluted with 0.1M sodium acetate buffer at pH 4.5, containing 0.1N NaCl. Dithiothreitol was added to this solution in sufficient quantity to produce a 25mM solution. This mixture was stirred for approximately 15 minutes at room temperature before concentrating and purifying on a Sephadex G-25 column eluted with 0.1N sodium phosphate at pH 7.5. Peroxidase (43 mg) was dissolved in 4 ml of 0.1N sodium phosphate at pH 7.5 containing 0.1N NaCl. To this were added 675 μL of 20mM SPDP and the resulting solution stirred for about 1 hour at which time the solution was applied to a Sephadex G-25 column and eluted with 0.1N sodium phosphate, pH 7.5. The derivatized peroxidase was obtained in the column void volume and concentrated to 2 ml. The peroxidase-SPDP was then combined with the derivatized antibody. This solution was concentrated to a total volume of 8 ml and allowed to react at room temperature, with stirring, for about 20 hours. The conjugate was isolated on a Sephadex G-100 column eluted with PBS.

Techniques for attaching antibodies or antigens to solid substrates are also well known in the art. (See: *Immobolizing enzymes, Antigens, Antibodies, and Peptides*, edited by Howard H. Weetall, Marcell Dekker Inc. (New York 1975) which is incorporated by reference herein.) For example, antibodies may be coupled covalently using glutaraldehyde to a silane derivative of borosilicate glass.

Other chemiluminescence cofactors which could also be used to induce a light response in the presence of peroxidase include isobutyraldehyde and oxygen.

Further suitable reagent systems are suggested by reactions (2) and (3) using different chemiluminescence catalysts:

$$FMNH_2 + O_2 + RCHO \xrightarrow{\text{Bacterial Luciferase}} \quad (2)$$

$$FMN + RCOOH + H_2 + h\nu$$

wherein $FMNH_2$ is reduced flavin mononucleotide, R is a straight carbon chain having from 8 to 12 carbons, and FMN is flavin mononucleotide.

$$Luciferin + ATP + O_2 \xrightarrow[Mg^{++}]{\text{Firefly Luciferase}} \quad (3)$$

$$Oxyluciferin + AMP + CO_2 + PPi + h\nu$$

wherein ATP is adenosine triphosphate, AMP is adenosine monophosphate, and PPi is an organic phosphate.

Briefly, an embodiment of the present invention includes a method for assaying fluid samples for an analyte including a member of a ligand-antiligand pair comprising the step of introducing a fluid sample, which may contain the analyte of interest, into a containment vessel containing reagent and having a first chamber and a second chamber. The reagent includes reagent ligand-antiligand pair members. One of the reagent ligand-antiligand pair members is restricted to the first chamber. The opposing reagent members include a label agent capable of detection. Sample analyte is allowed to compete for binding sites within reagent members allowing a portion of the labelled reagent member to diffuse through a blocking entity and into the second chamber in relation to the amount of analyte present in the sample. The label agent produces a detectable response in the second chamber which is monitored. The magnitude of the response is indicative of the concentration of the sample analyte.

The sample ligand-antiligand may include an antigen or antibody, a DNA strand which binds to a complementary strand, an enzyme which binds to a substrate or any other molecular species which selectively binds to another molecular species.

The blocking entity may include a membrane; however, other means may be applied as well. For example, if the detectable response is a light emission, a light screen or light blocking agent may be positioned between the first chamber and the detection means. Alternatively, the containment vessel may be formed to position the detection means so that light emissions outside the second chamber will not be detected.

A further embodiment of the present invention includes a sample device for assaying fluid samples potentially containing an analyte wherein said analyte includes a member of a ligand-antiligand pair. The sample device includes a containment vessel adapted to receive a fluid sample. The containment vessel contains reagent and has a first chamber, a second chamber and blocking means or a blocking entity. The reagent includes reagent members of a ligand-antiligand pair specific to the analyte of interest. One of the pair of reagent members is restricted to the first chamber. The opposing reagent member has a label agent capable of detection. The first chamber is in fluid communication with said second chamber with the blocking entity interposed therebetween allowing the label agent to be detected in the second chamber to the exclusion of the first chamber. The opposing label member and label agent assume a concentration in the second chamber in proportion to the amount of opposing reagent members conjugated to the reagent members restricted to the first chamber which is determined by the concentration of analyte in the sample.

The reagent members are preferably immobilized near the point at which the sample enters the first chamber in order to maximize contact with sample analyte. The first chamber provides a place for the competition reaction between the sample analyte and an analogous reagent member for limited binding sites. If sample analyte is present, some of the labelled opposing reagent members will be displaced and will diffuse to the second chamber where the label agent will be detected.

Preferably, the label agent is a chemiluminesence moiety. The second chamber must then provide the necessary cofactors for producing light in the presence of the light-labelled reagent member. It also necessarily must provide a means for permitting light detection, such as having at least one transparent surface in order that any light emitted within can be transmitted to an external detector.

In the case where peroxidase is a label agent and hydrogen peroxide is one of the cofactors, it is preferable to produce hydrogen peroxide in the immediate vicinity of the peroxidase-labelled reagent member and the means for detecting the light emission. Thus, a cofactor generating catalyst (such as glucose oxidase) and opposing members may be immobilized close together near a photomultiplier tube for detecting light emissions to optimize the chances of light emission and light detection.

The necessary cofactors can be supplied within the second chamber in dried or lyophilized form which is activated upon rehydration. Alternately, some or all of the cofactors can be produced in situ by cofactor generating catalysts. Again, the cofactor generating catalyst may be supplied in a dried or lyophilized form which is activated upon rehydration.

General considerations which will influence the form of cofactor used include the light label selected, chemical stability of the cofactors and the cofactor's stability to lyophilization. The choice will also depend upon the size of the cofactor and the ability to prevent its diffusion through the membrane back into the first chamber.

The blocking agent may include a permeable membrane. The permeable membrane serves to provide fluid communication between the first and second chambers while preventing unwanted mixing of the reagents. The membrane must have a pore size large enough to allow the light-labelled opposing reagent-member to diffuse into the second chamber. Further, the membrane must, at the same time, have a means for preventing at least one of the necessary cofactors from diffusing into the first chamber. Also, if the conjugated reagent members in the first chamber are not immobilized, the pore size must be small enough to prevent conjugated reagent members from diffusing into the second chamber. One purpose of the membrane therefore is to separate the first and second chambers to the extent that light emission occurs substantially solely in the second chamber.

Thus, an embodiment of the present invention includes a scavenger catalyst restricted to the first chamber. The scavenger catalyst can be restricted by the pore size of the permeable membrane, coupled to a larger molecule which itself is impermeable to the membrane, or by immobilization onto the permeable membrane. The scavenger catalyst deactivates cofactors which are small enough to pass through the pores into the first chamber. In the case of a hydrogen peroxide cofactor, for example, catalase can be immobilized on the membrane to convert the hydrogen peroxide to water and oxygen. In such a case, it is preferable to have the scavenger catalyst immobilized on the first chamber side of the membrane to lower the cofactor concentration in the first chamber, while at the same time allowing a high concentration in the second chamber.

Alternatively, a cofactor such as luminol may be coupled to a large molecule which is itself impermeable to the membrane to restrict light-producing reactions in the second chamber.

Suitable membrane or netting materials may include rigid uniform continuous meshes or nettings of polymeric material, such as meshes marketed under the trademark SPECTRAMESH or other filter membranes. Pore sizes will vary with the reagents used and those skilled in the art will accordingly be able to select the appropriate membrane which suits the needs of the particular assay being conducted.

The means for introducing the sample into the first chamber can include injection or diffusion into the first chamber. An embodiment of the present invention includes a sample membrane permeable to the analyte of interest. Reagent members conjugated with light-labelled opposing reagent members are immobilized on the sample membrane to allow the sample analyte to pass in close proximity to the conjugated reagent members where the sample may compete more effectively for the binding sites.

Both permeable membranes act to filter extraneous matter. However, any means can be used which provides enough sample to fill both the first and second chambers. The fluid communication between the chambers allows the sample to wet the reagents in the second chamber and initiate the necessary reactions to produce a light response in the presence of sample analyte.

The light response can be detected by any suitable detection device, such as a photomultiplier tube. This is preferably accomplished by detecting the light response transmitted through a transparent surface of the second chamber, but can also be accomplished through the use of a light-detecting probe imbedded within the second chamber.

Further, it is preferred that the label agent and cofactors be brought together in close proximity to the transparent surface or light-detecting probe. Thus, an embodiment of the present invention includes reagent members, specific to the light-labelled opposing reagent member, affixed to the transparent surface or on the light-detecting probe. The second chamber immobilized reagent members further immobilize light-labelled reagent ligands by conjugation. Cofactors or cofactor-generating catalysts may be immobilized in close proximity to the second chamber reagent members on or near the transparent surface to increase the likelihood that light-emitting reactions will occur close to the light-detecting probe. The present invention maintains its sensitivity even in turbid samples because the light-emitting reactions take place close to the light-detecting means or transparent surfaces.

Turning now to the Drawings, an embodiment of the invention will be described in greater detail in which the immunological pair member of interest is an antigen. The Drawings consist of three figures which schematically illustrate the operation of a sample device embodying features of the present invention. Peroxidase is the labelling agent which is coupled to a reagent antigen. The letter "A" generally designates antigen and "C" generally designates the chemiluminescence moiety acting as a labelling agent.

Figure 1:
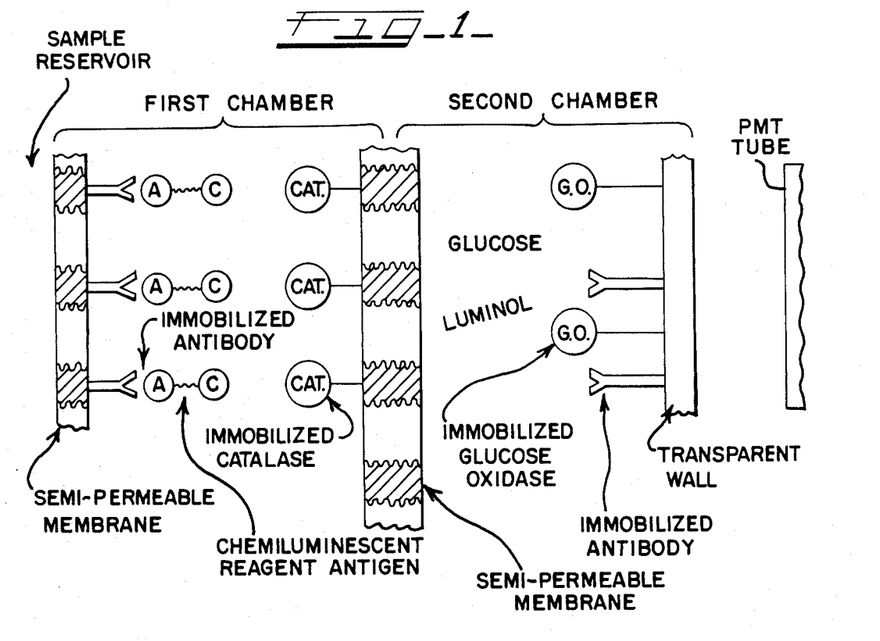

FIG. 1 depicts a sample device devoid of sample and in a dry static state. The sample device schematically illustrates a containment vessel which includes a sample reservoir and a first and a second chamber. The first and second chambers are separated by a first permeable membrane. A second permeable membrane separates the sample reservoir from the first chamber. The second chamber includes a transparent surface in optical communication with a photomultiplier tube (PMT).

The sample reservoir serves as a means for introducing sample into the first chamber. The antibodies, conjugated with light-labelled reagent antigens (A-C), are immobilized on the surface of the second membrane, thus placing them in a location where sample antigen (A), if present, will have the greatest possible opportunity to compete for the limited antibody binding sites. A scavenger catalyst (catalase) which catalyzes the reaction of hydrogen peroxide to water and oxygen, is immobilized on the first chamber side of the first permeable membrane. The second chamber contains cofactors or means to generate cofactors necessary to elicit a light response in the presence of the label agent, peroxidase. The cofactors or cofactor-generating means are provided in a dried or lyophylized form which are reconstituted upon contact with water.

Cofactors or cofactor-generating catalysts may be immobilized or allowed to exist in a free state. As illustrated, the second chamber includes a cofactor-generating catalyst, glucose oxidase (G.O.), immobilized on the transparent wall. Glucose oxidase generates hydrogen peroxide in the presence of glucose. Hydrogen peroxide is a cofactor necessary to generate chemiluminescence in the presence of the label agent, peroxidase. Glucose, necessary to generate hydrogen peroxide, is provided in dry form. A second cofactor, luminol, is also present in dried form in non-limiting amounts.

Immobilized in close proximity to the glucose oxidase on the transparent wall are antibodies specific to the light-labelled reagent antigens. The glucose oxidase and antibodies are immobilized on the transparent surface to place the source of the light emissions close to a transparent surface to minimize the effect of turbid sample fluids. A photomultiplier tube (PMT) is located in optical communication with the transparent surface to receive and amplify light signals generated by chemiluminescence reactions within the second chamber.

Figure 2:
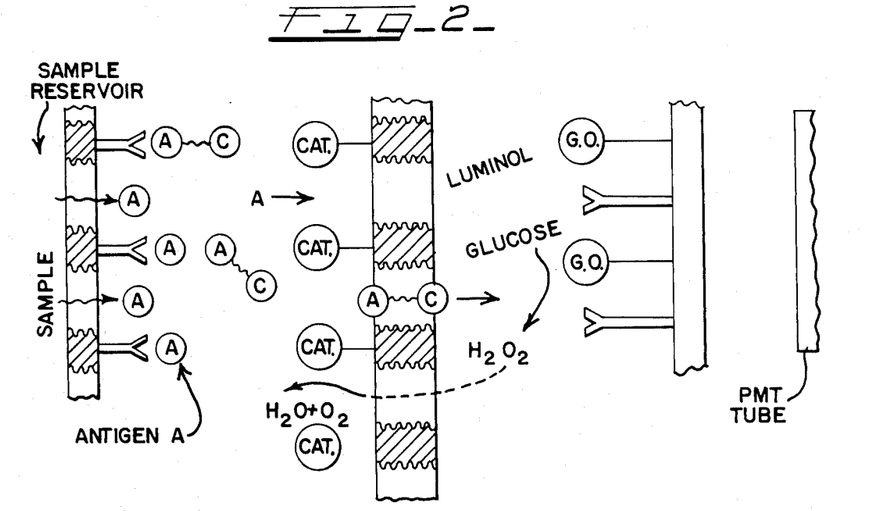

Turning now to FIG. 2, upon introduction of a fluid sample containing antigen into the sample reservoir, fluid begins to diffuse into the first chamber through the first membrane and then through the second membrane into the second chamber, thereby wetting the reagents and activating the system. Once wetted, the enzyme, glucose oxidase (G.O.), begins reacting with glucose to produce hydrogen peroxide within the second chamber.

At the same time, the scavenger enzyme catalase, immobilized on the second permeable membrane, is activated in the first chamber. The immobilized catalase prevents a significant buildup of hydrogen peroxide concentration in the first chamber by converting it to water and oxygen as the hydrogen peroxide passes through the membrane. Therefore, even though the other cofactor, luminol, may be present in the first chamber, light-emitting reactions in the first chamber are at most minimal.

Alternatively, the cofactor luminol and/or the scavenger enzyme catalase may be coupled to a large molecule which will not permit the entity to diffuse from their respective chambers through the first permeable membrane.

Antigens (A) pass into the first chamber from the sample reservoir through the second permeable membrane where the antigen competes with the light-labelled reagent antigen for the limited number of antibody binding sites. The number of light-labelled reagent antigens displaced by the sample antigens are related to the concentration of sample antigen. Some of the displaced light-labelled reagent antigens diffuse through the permeable membrane into the second chamber where they are exposed to all of the cofactors.

Figure 3:
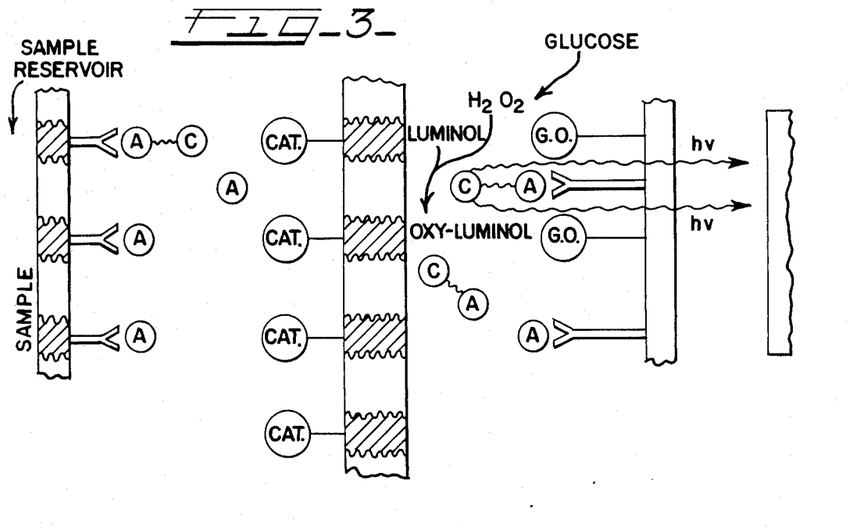

Turning now to FIG. 3, the light-labelled antigen is circulated within the sample medium into close proximity to the immobilized cofactor generator, glucose oxidase (G.O.). The light-labelled reagent antigens displaced from the first chamber attach to the immobilized antibodies. Although the light-labelled antigens compete for such antibody sites in the second chamber with non-labelled sample antigens, the concentration of the light-labelled antigen in the second chamber binding to the antibody sites is still dependent on the concentration of antigen in the original sample.

A light-emitting reaction occurs as hydrogen peroxide is produced by glucose oxidase (G.O.) and migrates to the peroxidase label agent in the presence of luminol. The light leaves the second chamber through the transparent wall where it is detected by the photomultiplier tube. The quanta of light detected is related to the number of chemiluminescence reactions taking place in the second chamber, which in turn is related to the number of light-labelled reagent antigens displaced from the first chamber. Hence, the light emission is related to the concentration of antigen in the sample which caused the initial displacement of the light-labelled reagent antigens.

The sample device can therefore be calibrated for the specific assay being conducted, permitting unknown antigen concentrations to be determined by the amount of chemiluminescence light emitted.

The light-emitting reactions take place in close proximity to the transparent wall where the light-labelled reagent antigen is conjugated on the immobilized antibody in the presence of cofactors. The light emitted by the reactions does not travel appreciable distances within the sample fluids and will therefore give readings, even though the sample fluid may be turbid.

The present apparatus is easily stored in a dried state and is readily adaptable to automated analysis equipment. The present apparatus and method require minimal skill and handling to provide a reliable assay technique.

Figure 4:
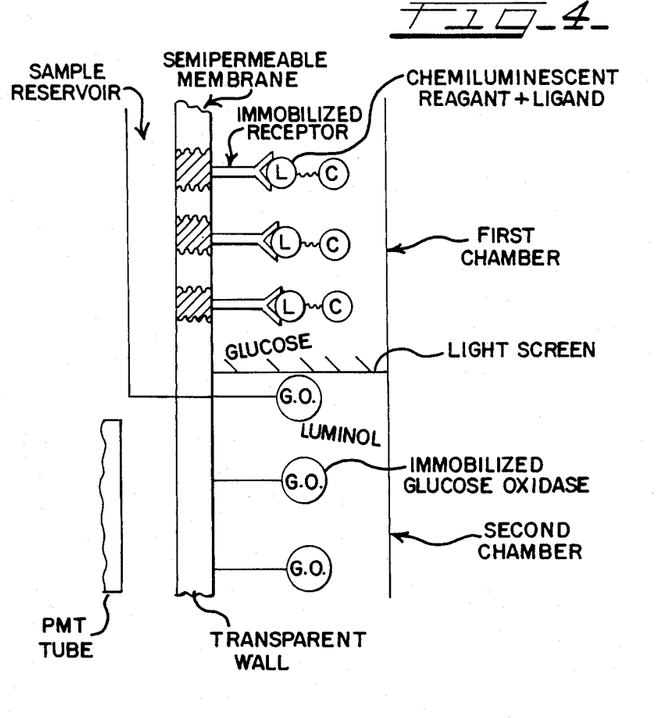
Figure 5:
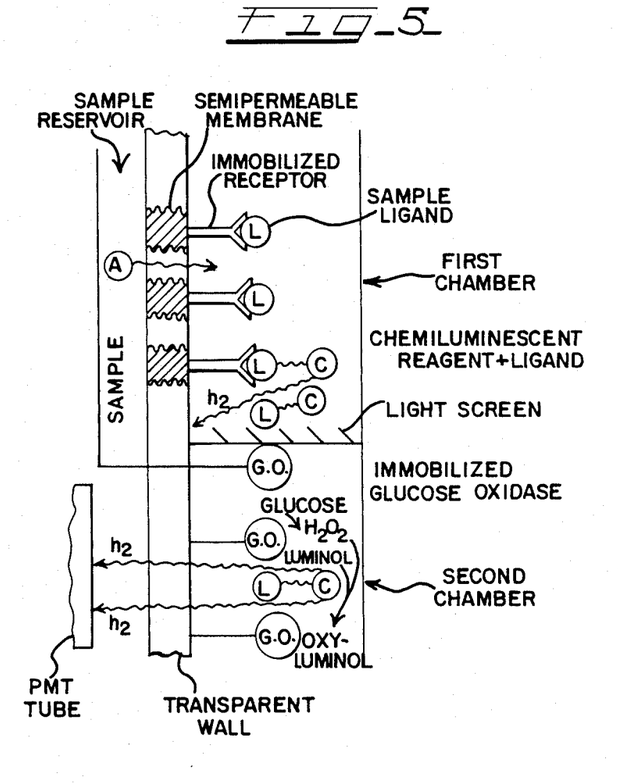

Turning now to FIGS. 4 and 5, an embodiment of the invention will be described in greater detail in which the analyte of interest is a member of a ligand-antiligand pair which may include, for example, antibody-antigen complexes, complementary strands of DNA or RNA, enzymes and enzyme-substrates, or a drug and a drug receptor. Peroxidase again is the labelling agent which is coupled to a reagent ligand. The letter "L" generally designates ligand and "C" generally designates the chemiluminescence moiety acting as a labelling agent.

FIG. 1 depicts a sample device devoid of sample and in a dry static state. The sample device schematically illustrates a containment vessel which includes a sample reservoir and a first and a second chamber. The first and second chambers are separated by a light screen. A permeable membrane separates the sample reservoir from the first chamber. The second chamber includes a transparent surface in optical communication with a photomultiplier tube (PMT).

The sample reservoir serves as a means for introducing sample into the first chamber. The antiligands, conjugated with light-labelled reagent antigens (L–C), are immobilized on the surface of the membrane, thus placing them in a location where sample ligand (L), if present, will have the greatest possible opportunity to compete for the limited binding sites. The second chamber contains cofactors or means to generate cofactors necessary to elicit a light response in the presence of the label agent, peroxidase. The cofactors or cofactor-generating means are provided in a dried or lyophilized form which are reconstituted upon content with water.

Cofactors or cofactor-generating catalysts may be immobilized or allowed to exist in a free state. As illustrated, the second chamber includes a cofactor-generating catalyst, glucose oxidase (G.O.), immobilized on the transparent wall. Glucose oxidase generates hydrogen peroxide in the presence of glucose. Hydrogen peroxide is a cofactor necessary to generate chemiluminescence in the presence of the label agent, peroxidase. Glucose, necessary to generate hydrogen peroxide, is provided in dry form. A second cofactor, luminol, is also present in dried form in non-limiting amounts.

Glucose oxidase is immobilized on the transparent surface to place the light-emitting reaction as close to a transparent surface to minimize the effect of turbid sample fluids. A photomultiplier tube (PMT) is located in optical communication with the transparent surface to receive and amplify light signals generated by chemiluminescent reactions within the second chamber.

Upon introduction of a fluid sample containing analyte ligand into the sample reservoir, fluid begins to diffuse into the first chamber through the first membrane and into the second chamber, thereby wetting the reagents and activating the system. Once wetted, the enzyme, glucose oxidase (G.O.), begins reacting with glucose to produce hydrogen peroxide within the second chamber.

Analyte ligands (L) pass into the first chamber from the sample reservoir through the permeable membrane where the analyte ligands compete with the light-labelled reagent ligands for the limited number of binding sites on the immobilized receptor or antiligands. The number of light-labelled reagent ligands displaced by the sample analyte ligand will be proportional to the concentration of sample ligand. Some of the displaced light-labelled reagent ligands will diffuse into the second chamber where they will be exposed to all of the cofactors.

Turning now to FIG. 5, the light-labelled ligand is circulated within the sample medium into close proximity to the immobilized cofactor generator, glucose oxidase (G.O.). The concentration of the light-labelled ligand in the second chamber is dependent on the concentration of analyte ligand in the original sample.

A light-emitting reaction occurs as hydrogen peroxide is produced by glucose oxidase (G.O.) and migrates to the peroxidase label agent in the presence of luminol. The light leaves the second chamber through the transparent wall where it is detected by the photomultiplier tube. The quanta of light detected is related to the number of chemiluminescence reactions taking place in the second chamber, which in turn is related to the number of light-labelled reagent ligands displaced from the first chamber. Hence, the light emission is related to the concentration of analyte ligand in the sample which caused the initial displacement of the light-labelled reagent ligand.

The sample device can therefore be calibrated for the specific assay being conducted, permitting unknown analyte ligand concentrations to be determined by the amount of chemiluminescence light emitted.

Cofactors such as glucose and luminol may be allowed to exist freely in both chambers because light-emitting reactions caused by chemiluminescence reagent ligands in the first chamber, even bound to receptor ligand, are blocked by the light screen. The light screen may take many forms. For example, the light screen may include the geometry of the containment vessel which positions the photomultiplier tube in a position relative to the first chamber where light emissions in the first chamber are not detected.

Thus, while the present invention has been described and illustrated, it will be apparent to those skilled in the art that many variations and modifications can be made without departing from the purview of the appended claims and without departing from the teachings and scope of the present invention.

We claim:

1. A sample device for assaying fluid samples potentially containing an analyte, wherein said analyte includes a member of a liquid-antiligand pair, comprising: a containment vessel, adapted to receive a fluid sample, and containing a reagent, said vessel having a first chamber, a second chamber and cofactor blocking means, wherein said reagent includes a cofactor source and reagent members of a liquid-antiligand pair specific to the analyte of interest, one of said reagent members being restricted in said first chamber, the opposing reagent member having a label agent, said cofactor source providing cofactors which participate in a reaction with said label agent, which reaction is detectable, said first chamber being in fluid communication with said second chamber, said cofactor blocking means interposed between said first and second chambers limiting the presence of said cofactor to said second chamber, allowing said label agent to be detected in said second chamber to the exclusion of said first chamber, said opposing reagent member having a label agent assuming a concentration in said second chamber in relation to the concentration of analyte.

2. The sample device of claim 1 wherein said label agent is a chemiluminescence moiety which participates in light-producing reactions.

3. The sample device of claim 2 further comprising means for detecting light within said second chamber.

4. The sample device of claim 3 wherein said means for detecting light within said second chamber comprises at least one transparent surface.

5. The sample device of claim 2 wherein said cofactor source includes a cofactor-generating catalyst.

6. The sample device of claim 5 wherein the cofactor-generating catalyst is immobilized.

7. The sample device of claim 2 wherein blocking means is a permeable membrane.

8. The sample device of claim 7 wherein said blocking means is a cofactor scavenger catalyst.

9. The sample device of claim 8 wherein said cofactor scavenger catalyst is immobilized on said membrane.

10. The sample device of claim 9 wherein said scavenger catalyst is immobilized on the side of the membrane within the first chamber.

11. The sample device of claim 5 wherein the second chamber contains a substrate for producing a cofactor in the presence of the cofactor-generating catalyst.

12. The sample device of claim 1 wherein the reagent members in the first chamber are conjugated with said opposing reagent members.

13. The sample device of claim 7 wherein said reagent members in the first chamber are affixed to macromolecules unable to diffuse through said membrane.

14. The sample device of claim 1 further comprising means for introducing a sample into the first chamber wherein said analyte members are able to enter said first chamber in close proximity to said reagent members restricted to said first chamber.

15. The sample device of claim 14 wherein said means for introducing a sample comprises a reservoir in fluid communication with said first chamber and a sample membrane separating said reservoir from said first chamber to which reagent members restricted to said first chamber are affixed.

16. The sample device of claim 4 wherein the cofactor source in the second chamber is immobilized on said transparent surface.

17. The sample device of claim 4 wherein the transparent surface of the second chamber has immobilized reagent members specific to said labelled reagent member.

18. The sample device of claim 2 wherein said label agent is peroxidase.

19. The sample device of claim 5 wherein the cofactor-generating catalyst is glucose oxidase.

20. The sample device of claim 5 wherein glucose oxidase is immobilized on a transparent surface.

21. The sample device of claim 8 wherein the scavenger catalyst is catalase.

22. A sample device for assaying fluid samples potentially containing an analyte, wherein said analyte is a member of an immunological pair, comprising:

a containment vessel adapted to receive a fluid sample, and containing a reagent, said vessel having a first chamber, a second chamber, and cofactor blocking means, wherein said reagent includes a cofactor source and reagent members of an immunological pair specific to the analyte of interest, said reagent immunological pair members including one reagent member restricted to said first chamber, the opposing reagent member having a chemiluminescence label agent, said cofactor source providing cofactors which participate in a reaction with said chemiluminescent label agent to produce a detectable light response, said first chamber being in fluid communication with said second chamber, said cofactor blocking means allowing light detection of said chemiluminescent label agent in said second chamber to the exclusion of said first chamber, said opposing reagent member having a chemiluminescent label agent assuming a concentration in said second chamber in relation to the concentration of the analyte.

23. The sample device of claim 22 further comprising means for introducing sample into the first chamber wherein said sample analyte enters said first chamber in close proximity to said reagent members restricted to said first chamber.

24. The sample device of claim 23 wherein said means for introducing sample is a sample reservoir in communication with said first chamber, said sample reservoir separated from said first chamber by permeable membrane on which said reagent members within the first chamber are immobilized.

25. The sample device of claim 22 wherein said blocking means includes a permeable membrane.

26. The sample device of claim 25 wherein said permeable membrane is a scavenger catalyst.

27. A method for assaying a fluid sample potentially containing an analyte of interest, wherein said analyte is a member of a liquid-antiligand pair, comprising:

(a) introducing a fluid sample potentially containing the analyte into a containment vessel containing a reagent and having a first chamber, a second chamber, and cofactor blocking means, wherein said reagent includes a cofactor source and reagent members of a ligand-antiligand pair specific to the analyte of interest, including one reagent member restricted to said first chamber, the opposing reagent member having a label agent, said cofactor source providing cofactors which participate in a reaction with said label agent which reaction produces a detectable response, wherein said analyst may compete with said reagent ligand-antiligand pair and allow said labelled opposing reagent to enter said second chamber, said cofactor blocking means limiting the presence of said cofactor to said second chamber and allowing said label agent to be detected in said second chamber to the exclusion of said first chamber, said opposing reagent member having a label agent assuming a concentration in said second chamber in relation to the concentration of analyte; and, (b) monitoring said second chamber for said label agent.

28. The method of claim 27 wherein said reagent members of a ligand-antiligand pair are conjugated prior to the introduction of said fluid sample.

29. The method of claim 27 wherein said label agent is peroxidase.

30. The method of claim 28 wherein said cofactor source is a cofactor-generating catalyst.

31. The method of claim 27 wherein cofactor blocking means prevents said cofactor from entering said first chamber.

32. The method of claim 27 wherein said cofactor blocking means deactivates said cofactor as said cofactor enters said first chamber.

33. The method of claim 27 wherein said label agent participates in reactions which produce a light emission.

34. The method of claim 33 wherein said cofactor is selected from the group of cofactors consisting essentially of hydrogen peroxide, luminol, glucose, and glucose oxidase.

35. The method of claim 27 wherein said blocking means is a light screen.

36. The method of claim 27 wherein said blocking means is label direction means positioned relative to said first chamber to detect label in said second chamber to the exclusion of said first chamber.

37. The sample device of claim 7 wherein said cofactor is associated with a macromolecule within said second chamber and is impermeable to said permeable membrane.

* * * * *

UNITED STATES PATENT OFFICE
CERTIFICATE OF CORRECTION

Patent No. 4,859,583  Dated August 22, 1989

Inventor(s) Michael J. Heller and Larry E. Morrison

It is certified that error appears in the above-identified patent and that said Letters Patent is hereby corrected as shown below:

| Column | Line | |
|---|---|---|
| 2 | 53 | "heterogeneous" should read --heterogenous-- |
| 2 | 67 | "homogeneous" should read --hemogenous-- |
| 4 | 66 | "phosphate buffered" should read --phosphate-buffered-- |
| 6 | 31 | "-tween allowing" should read --tween, allowing-- |
| 10 | 53 | "content" should read --contact-- |
| 13 | 19 | "chemiluminescence" should read --chemiluminescent-- |
| 13 | 19 | "cofactor" should read --cofactors-- |
| 14 | 6 | "cofactor" should read --cofactors-- |
| 14 | 9 | "analyst" should read --analyte-- |
| 14 | 44 | "direction" should read --detection-- |

Signed and Sealed this

Twenty-third Day of October, 1990

Attest:

HARRY F. MANBECK, JR.

*Attesting Officer*   *Commissioner of Patents and Trademarks*